United States Patent
Echols

(10) Patent No.: US 11,672,473 B2
(45) Date of Patent: Jun. 13, 2023

(54) PAIN LEVEL INDICATOR ASSEMBLY

(71) Applicant: Khamra Echols, Dallas, TX (US)

(72) Inventor: Khamra Echols, Dallas, TX (US)

(*) Notice: Subject to any disclaimer, the term of this patent is extended or adjusted under 35 U.S.C. 154(b) by 805 days.

(21) Appl. No.: 16/731,151

(22) Filed: Dec. 31, 2019

(65) Prior Publication Data
US 2021/0196190 A1 Jul. 1, 2021

(51) Int. Cl.
A61B 5/00 (2006.01)

(52) U.S. Cl.
CPC .......... A61B 5/4824 (2013.01); A61B 5/6826 (2013.01); A61B 5/742 (2013.01); A61B 5/7405 (2013.01); A61B 5/7465 (2013.01)

(58) Field of Classification Search
CPC ... A61B 5/4824; A61B 5/6826; A61B 5/7405; A61B 5/742; A61B 5/7465
USPC ...................................................... 340/573.1
See application file for complete search history.

(56) References Cited

U.S. PATENT DOCUMENTS

| 4,810,996 | A | 3/1989 | Glen | |
|---|---|---|---|---|
| 5,018,526 | A * | 5/1991 | Gaston-Johansson | A61B 90/90 600/300 |
| D375,748 | S | 11/1996 | Hailman | |
| 6,551,103 | B2 | 4/2003 | Gottfried | |
| 9,105,174 | B2 | 8/2015 | Harris | |
| 9,737,269 | B2 | 8/2017 | Moreno | |
| 2006/0055544 | A1 | 3/2006 | Morguelan | |
| 2007/0034213 | A1* | 2/2007 | Poisner | A61B 5/4824 607/46 |
| 2011/0066078 | A1 | 3/2011 | Sarvazyan | |
| 2015/0265208 | A1* | 9/2015 | Addison | A61B 5/0836 600/301 |
| 2016/0198996 | A1* | 7/2016 | Dullen | A61B 5/4848 600/595 |
| 2018/0263560 | A1* | 9/2018 | Bakker | A61B 5/4884 |
| 2019/0150851 | A1* | 5/2019 | Clark | A61B 5/024 |
| 2020/0203010 | A1* | 6/2020 | Durlach | A61G 7/0528 |
| 2020/0237291 | A1* | 7/2020 | Sundaram | A61B 5/1032 |
| 2020/0275886 | A1* | 9/2020 | Mason | A61B 5/1071 |
| 2022/0355646 | A1* | 11/2022 | Yamamoto | B60H 1/00985 |

FOREIGN PATENT DOCUMENTS

WO WO0185085 11/2001

* cited by examiner

Primary Examiner — Omar Casillashernandez

(57) ABSTRACT

A pain level indicator assembly includes an increase control that is holdable by a patient and a decrease control that is holdable by the patient. A display unit is provided and the display unit is positionable in a prominent position in a healthcare environment to be visible to a caregiver. The display unit is in remote communication with each of the increase control and the decrease control. Additionally, the display unit displays gauge indicia comprising a pain meter ranging between a predetermined negative integer and a predetermined positive integer. The display unit is actuated to display a point along the gauge indicia to communicate the patient's pain level to the caregiver.

13 Claims, 4 Drawing Sheets

PAIN LEVEL INDICATOR ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to indicator devices and more particularly pertains to a new indicator device for non-verbally communicating pain level between a patient and a caregiver.

(2) Description of Related Art Including Information Disclosed Under 37 CFR 1.97 and 1.98

The prior art relates to indicator devices. The prior art discloses a variety of devices to accomplish non verbal communication between a patient and a caregiver. The devices employ a variety of alerts, including audible alerts and visual alerts. Additionally, the prior art discloses an electronic means of communicating patient comfort data that includes an internet connection and database servers. The prior art discloses a pain meter which includes a remote control that is wired to a display unit. Additionally, the prior art discloses a pain level indicator that is pressure sensitive and emits an audible alarm when exposed to a trigger pressure from being squeezed by a patient.

BRIEF SUMMARY OF THE INVENTION

An embodiment of the disclosure meets the needs presented above by generally comprising an increase control that is holdable by a patient and a decrease control that is holdable by the patient. A display unit is provided and the display unit is positionable in a prominent position in a healthcare environment to be visible to a caregiver. The display unit is in remote communication with each of the increase control and the decrease control. Additionally, the display unit displays gauge indicia comprising a pain meter ranging between a predetermined negative integer and a predetermined positive integer. The display unit is actuated to display a point along the gauge indicia to communicate the patient's pain level to the caregiver.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
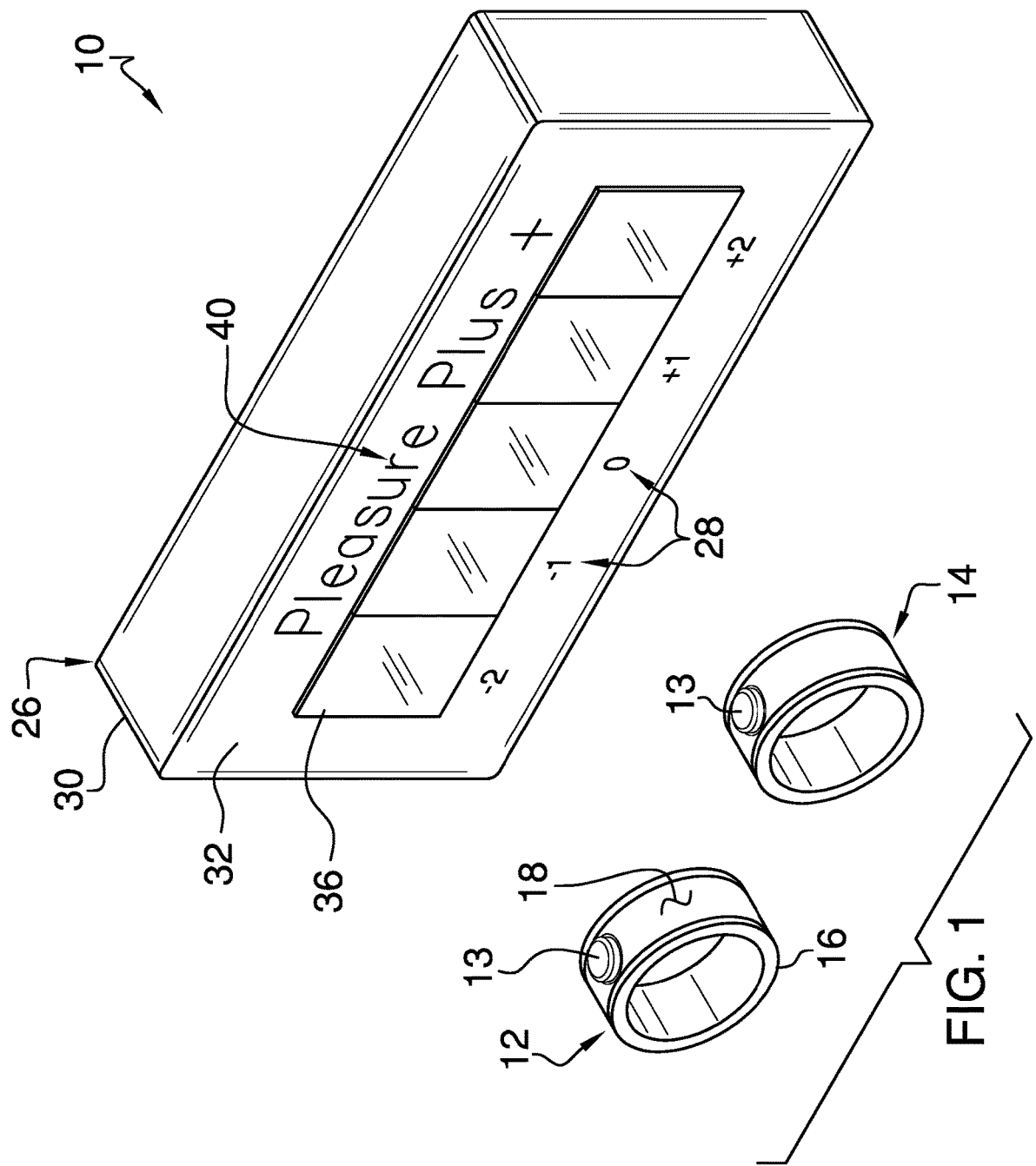
FIG. 1 is a perspective view of a pain level indicator assembly according to an embodiment of the disclosure.
Figure 2:
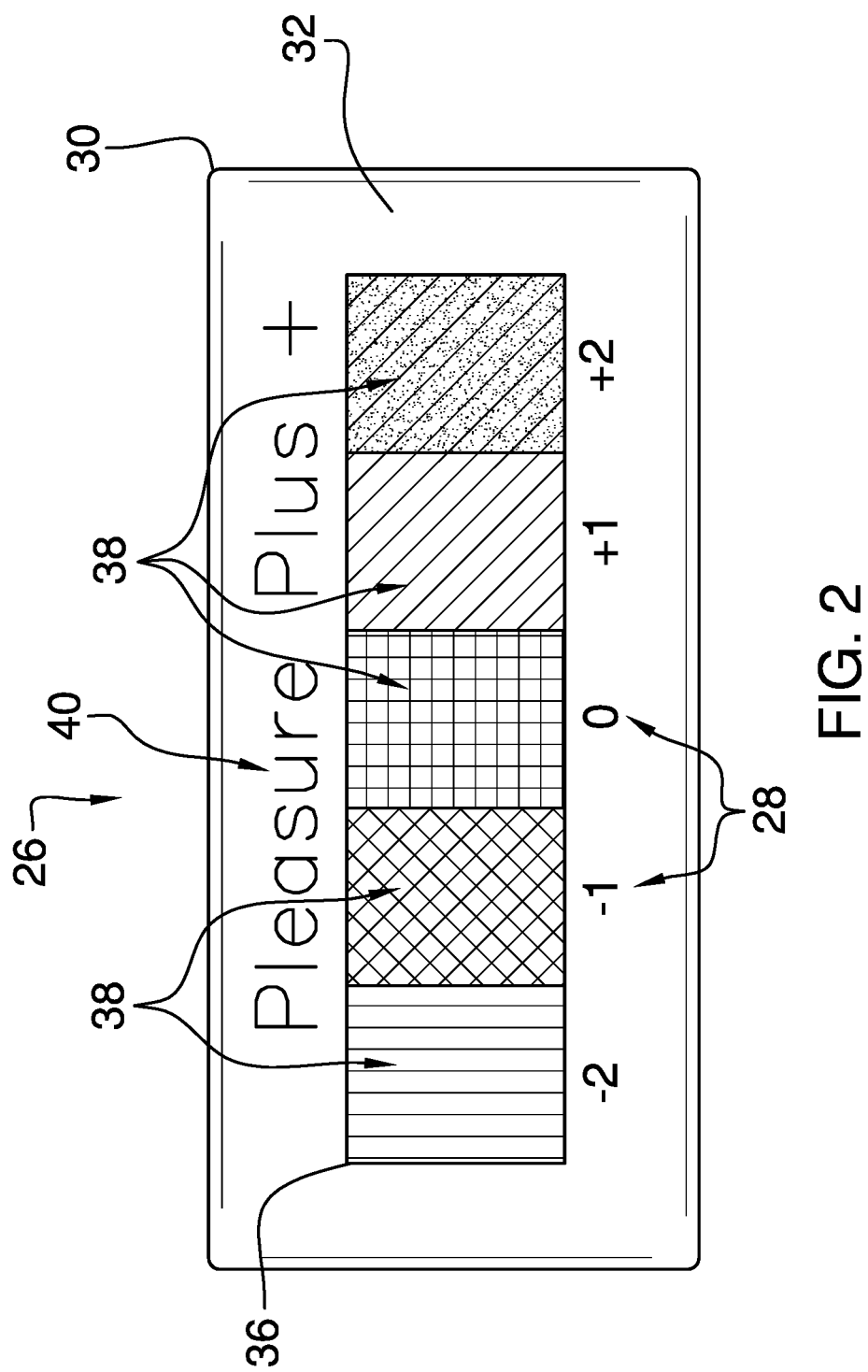
FIG. 2 is a front view of a display unit of an embodiment of the disclosure.
Figure 3:
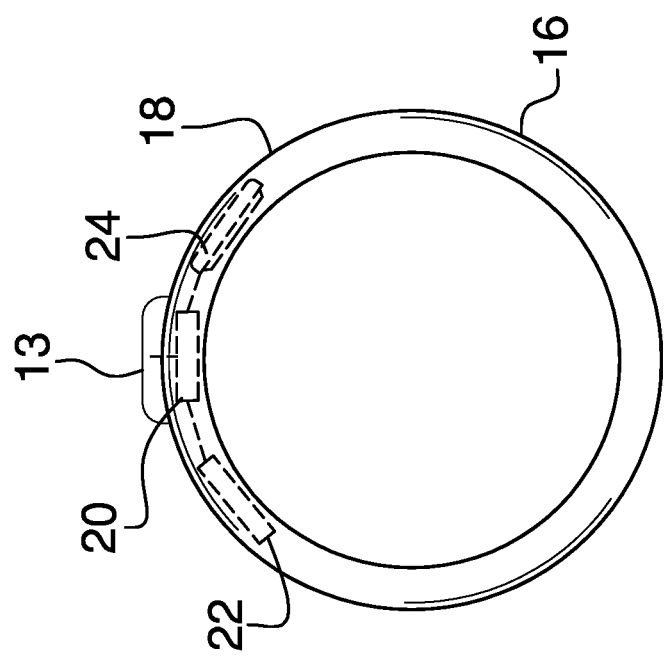
FIG. 3 is a front phantom view of a ring of an embodiment of the disclosure.
Figure 4:
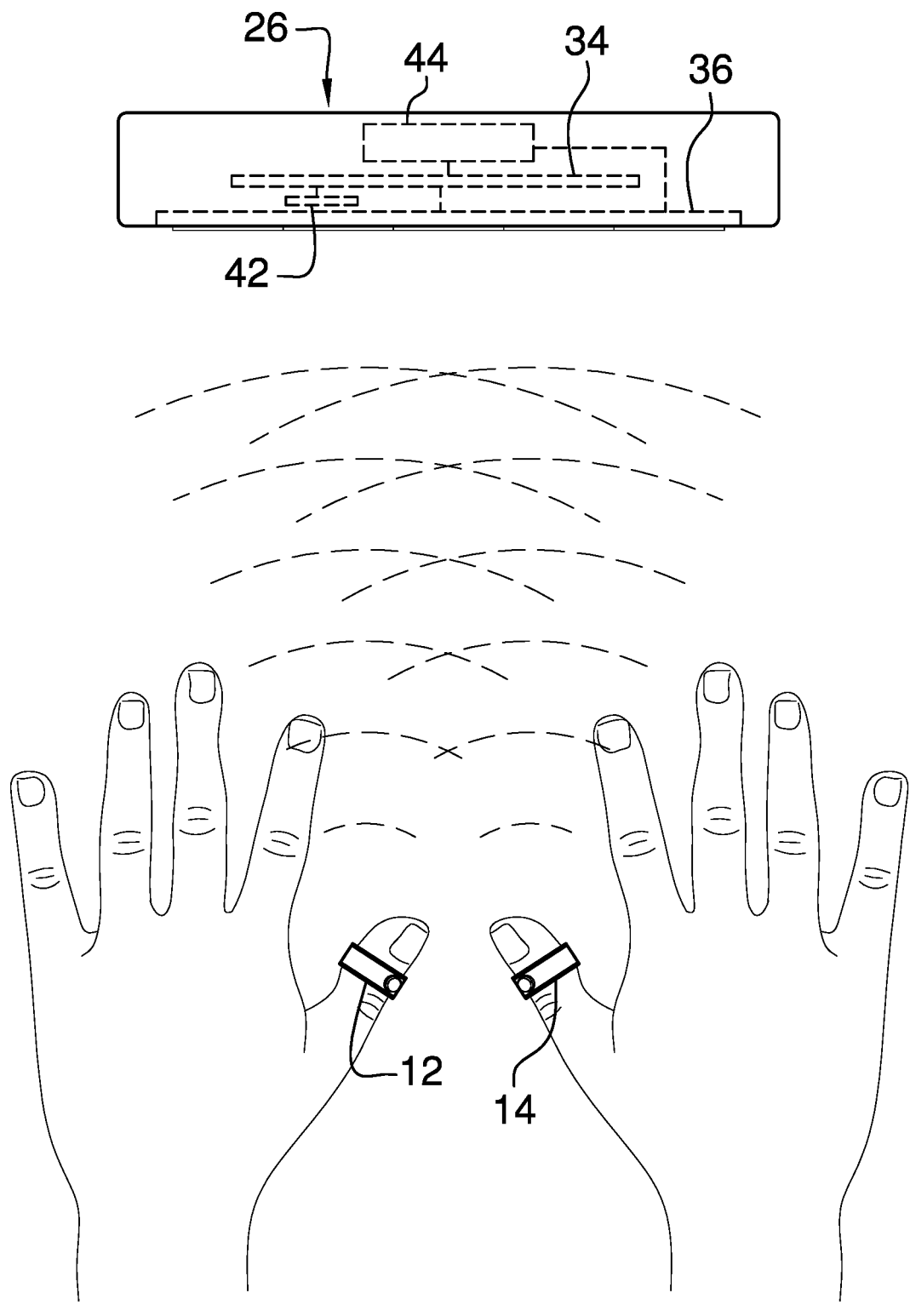
FIG. 4 is a perspective in-use view of an embodiment of the disclosure.

With reference now to the drawings, and in particular to FIGS. 1 through 4 thereof, a new indicator device embodying the principles and concepts of an embodiment of the disclosure and generally designated by the reference numeral 10 will be described.

As best illustrated in FIGS. 1 through 4, the pain level indicator assembly 10 generally comprises an increase control 12 that is holdable by a patient. The patient may be a person getting a therapeutic massage, a person undergoing a surgical procedure with local anesthetic, a person in hospice or any other type of patient. The increase control 12 broadcasts an increase signal when a button 13 on the increase control 12 is depressed. In this way the increase control 12 facilitates the patient to non-verbally communicate an increased level of pain.

A decrease control 14 is provided and the decrease control 14 is holdable by the patient. The decrease control 14 broadcasts a decrease signal when a button 13 on the decrease control 14 is depressed. In this way the decrease control 14 facilitates the patient to non-verbally communicate a decreased level of pain. Thus, the patient does not have to rely on verbal communication, regardless of whether the patient is a verbal patient or a non-verbal patient.

Each of the increase control 12 and the decrease control 14 comprise a ring 16 that is wearable around one of the patient's fingers, preferably the thumb. The ring 16 has an outwardly facing surface 18 and the ring 16 corresponding to each of the increase control 12 and the decrease control 14 is positioned on respective ones of the patient's hands. The increase control 12 and the decrease control 14 each includes a remote control circuit 20 that is positioned within the ring 16 and the remote control circuit 20 receives a broadcast input. The button 13 corresponding to each of the increase control 12 and the decrease control 14 is movably positioned on the outwardly facing surface 18 of the ring 16 that corresponds to the increase control 12 or the decrease control 14. The button 13 is electrically coupled to the remote control circuit 20. Moreover, the remote control circuit 20 receives the broadcast input when the button 13 is depressed and released.

Each of the increase control 12 and the decrease control 14 includes a transmitter 22 that is positioned in the ring 16. The transmitter 22 is electrically coupled to the remote control circuit 20. The transmitter 22 corresponding to the increase control 12 broadcasts the increase signal when the remote control circuit 20 receives the broadcast input. Additionally, the transmitter 22 corresponds to the decrease control 14 broadcasts the decrease signal when the remote control circuit 20 receives the broadcast input. The transmitter 22 may comprise a radio frequency transmitter or the like. Each of the increase control 12 and the decrease control 14 includes a remote power supply 24 that is integrated into the ring 16. The remote power supply 24 is electrically coupled to the remote control circuit 20 and the remote power supply 24 comprising at least one battery.

A display unit 26 is provided and the display unit 26 is positionable in a prominent position in a healthcare environment such that the display unit 26 is visible to a caregiver. The display unit 26 is in remote communication with each of the increase control 12 and the decrease control 14. The display unit 26 displays gauge indicia 28 comprising a pain meter ranging between a predetermined negative integer and a predetermined positive integer. In this way the display unit 26 visually communicates a level of pain to the caregiver. The display unit 26 is actuated to display 36 an increasing integer each time the display unit 26 receives the increase signal. Additionally, the display unit 26 is actuated to display 36 a decreasing integer each time the display unit 26 receives the decrease signal.

The display unit 26 comprises a housing 30 that has a front wall 32 and the housing 30 is positioned such that the front wall 32 is visible to the caregiver. A base control circuit 34 is positioned in the housing 30 and the base control circuit 34 receives a decrease input and an increase input. A display 36 is coupled to the front wall 32 and the display 36 is electrically coupled to the base control circuit 34. Additionally, the display 36 may comprise a plurality of light emitters, a LED or any other type of electronic display 36 that can display a gauge.

The display 36 is divided into a plurality of sections 38 that is laterally distributed along the front wall 32. Each of the sections 38 is assigned to a respective one of the positive or negative integers. Respective sections 38 are turned on when the base control circuit 34 receives the decrease input or the increase input. In this way the display 36 visually communicates the patient's pain level to the caregiver. As is most clearly shown in FIGS. 1 and 2, the gauge may range between −2.0 and +2.0, including zero. Additionally, word indicia 40 may be printed on the front wall 32 of the housing 30 and the word indicia 40 may comprise "pleasure plus +".

The display unit 26 includes a receiver 42 that is coupled to the housing 30 and the receiver 42 is electrically coupled to the base control circuit 34. The receiver 42 is in wireless communication with the transmitter 22 and the receiver 42 receives the decrease signal and the increase signal. Thus, the base control circuit 34 receives the decrease input when the receiver 42 receives the decrease signal. Additionally, the base control circuit 34 receives the increase input when the receiver 42 receives the increase signal. The receiver 42 may comprise a radio frequency receiver or the like. The display unit 26 includes a base power supply 44 that is positioned in the housing 30, the base power supply 44 is electrically coupled to the base control circuit 34 and the base power supply 44 comprises at least one battery.

In use, the patient wears each of the increase control 12 and the decrease control 14 on each of the patient's hands. The patient depresses the button 13 on the decrease control 14 the required number of times to actuate the display 36 to display the desired decreasing level of pain. Conversely, the patient depresses the button 13 on the increase control 12 the required number of times to actuate the display 36 to display the desired increasing level of pain. In this way the patient can non-verbally communicate their pain level to the caregiver. Thus, the caregiver can immediately make the necessary adjustments for making the patient more comfortable, if necessary. The increase control 12 and the decrease control 14 are removed from the patient when the caregiver is finished with the patient.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pain level indicator assembly being configured to facilitate a patient to visually communicate their pain level to a caregiver, said assembly comprising:
  an increase control being holdable by a patient, said increase control broadcasting an increase signal when a button on said increase control is depressed wherein said increase control is configured to facilitate the patient to non verbally communicate an increased level of pain;
  a decrease control being holdable by the patient, said decrease control broadcasting a decrease signal when a button on said decrease control is depressed wherein said decrease control is configured to facilitate the patient to non verbally communicate a decreased level of pain;
  a display unit being positionable in a prominent position in a healthcare environment wherein said display unit is configured to be visible to a caregiver, said display unit being in remote communication with each of said increase control and said decrease control, said display unit displaying gauge indicia comprising a pain meter ranging between a predetermined negative integer and a predetermined positive integer wherein said display unit is configured to visually communicate a level of pain to the caregiver, said display unit being actuated to display an increasing integer each time said display unit receives said increase signal, said display unit being actuated to display a decreasing integer each time said display unit receives said decrease signal; and wherein each of said increase control and said decrease control comprises a ring that is wearable around one of the patient's fingers, said ring having an outwardly facing surface, said ring corresponding to each of said increase control and said decrease control being positioned on respective ones of the patient's hands.

2. The assembly according to claim 1, wherein each of said increase control and decease control comprises a remote control circuit being positioned within said ring, said remote control circuit receiving a broadcast input.

3. The assembly according to claim 2, wherein each of said increase control and said decrease control comprises said button corresponding to each of said increase control and said decrease control being movably positioned on said outwardly facing surface of said ring that corresponds to said increase control or said decrease control, said button being electrically coupled to said remote control circuit, said remote control circuit receiving said broadcast input when said button is depressed and released.

4. The assembly according to claim 3, wherein each of said increase control and said decrease control comprises a transmitter being positioned in said ring, said transmitter being electrically coupled to said remote control circuit, said transmitter corresponding to said increase control broadcasting said increase signal when said remote control circuit receives said broadcast input, said transmitter corresponding to said decrease control broadcasting said decrease signal when said remote control circuit receives said broadcast input.

5. The assembly according to claim 4, wherein each of said increase control and said decrease control comprises a remote power supply being integrated into said ring, said remote power supply being electrically coupled to said remote control circuit, said remote power supply comprising at least one battery.

6. The assembly according to claim 4, wherein said display unit comprises a housing having a front wall, said housing being positioned such that said front wall is visible to the caregiver.

7. The assembly according to claim 6, wherein said display unit comprises a base control circuit being positioned in said housing, said base control circuit receiving a decrease input and an increase input.

8. The assembly according to claim 7, wherein said display unit comprises a display being coupled to said front wall, said display being electrically coupled to said base control circuit.

9. The assembly according to claim 8, wherein said display is divided into a plurality of sections being laterally distributed along said front wall, each of said sections being assigned to a respective one of the positive or negative integers.

10. The assembly according to claim 9, wherein respective ones of said sections being turned on when said base control circuit receives said decrease input or said increase input wherein said display is configured to visually communicate the patient's pain level to the caregiver.

11. The assembly according to claim 10, wherein said display unit includes a receiver being coupled to said housing, said receiver being electrically coupled to said base control circuit, said receiver being in wireless communication with said transmitter, said receiver receiving said decrease signal and said increase signal, said base control circuit receiving said decrease input when said receiver receives said decrease signal, said base control circuit receiving said increase input when said receiver receives said increase signal.

12. The assembly according to claim 7, wherein said display unit includes a base power supply being positioned in said housing, said base power supply being electrically coupled to said base control circuit, said base power supply comprising at least one battery.

13. A pain level indicator assembly being configured to facilitate a patient to visually communicate their pain level to a caregiver, said assembly comprising:

an increase control being holdable by a patient, said increase control broadcasting an increase signal when a button on said increase control is depressed wherein said increase control is configured to facilitate the patient to non verbally communicate an increased level of pain;

a decrease control being holdable by the patient, said decrease control broadcasting a decrease signal when a button on said decrease control is depressed wherein said decrease control is configured to facilitate the patient to non verbally communicate a decreased level of pain, each of said increase control and said decrease control comprising:

a ring being wearable around one of the patient's fingers, said ring having an outwardly facing surface, said ring corresponding to each of said increase control and said decrease control being positioned on respective ones of the patient's hands;

a remote control circuit being positioned within said ring, said remote control circuit receiving a broadcast input;

said button corresponding to each of said increase control and said decrease control being movably positioned on said outwardly facing surface of said ring that corresponds to said increase control or said decrease control, said button being electrically coupled to said remote control circuit, said remote control circuit receiving said broadcast input when said button is depressed and released;

a transmitter being positioned in said ring, said transmitter being electrically coupled to said remote control circuit, said transmitter corresponding to said increase control broadcasting said increase signal when said remote control circuit receives said broadcast input, said transmitter corresponding to said decrease control broadcasting said decrease signal when said remote control circuit receives said broadcast input; and a remote power supply being integrated into said ring, said remote power supply being electrically coupled to said remote control circuit, said remote power supply comprising at least one battery; and a display unit being positionable in a prominent position in a healthcare environment wherein said display unit is configured to be visible to a caregiver, said display unit being in remote communication with each of said increase control and said decrease control, said display unit displaying gauge indicia comprising a pain meter ranging between a predetermined negative integer and a predetermined positive integer wherein said display unit is configured to visually communicate a level of pain to the caregiver, said display unit being actuated to display an increasing integer each time said display unit receives said increase signal, said display unit being actuated to display a decreasing integer each time said display unit receives said decrease signal, said display unit comprising:

a housing having a front wall, said housing being positioned such that said front wall is visible to the caregiver;

a base control circuit being positioned in said housing, said base control circuit receiving a decrease input and an increase input;

a display being coupled to said front wall, said display being electrically coupled to said base control circuit, said display being divided into a plurality of sections being laterally distributed along said front wall, each of said sections being assigned to a respective one of the positive or negative integers, respective ones of said sections being turned on when said base control circuit receives said decrease input or said increase input wherein said display is configured to visually communicate the patient's pain level to the caregiver;

a receiver being coupled to said housing, said receiver being electrically coupled to said base control circuit, said receiver being in wireless communication with said transmitter, said receiver receiving said decrease signal and said increase signal, said base control circuit receiving said decrease input when said receiver receives said decrease signal, said base control circuit receiving said increase input when said receiver receives said increase signal; and a base power supply being positioned in said housing, said base power supply being electrically coupled to said base control circuit, said base power supply comprising at least one battery.

* * * * *